United States Patent [19]

de Groot et al.

[11] 4,345,978
[45] Aug. 24, 1982

[54] METHOD AND APPARATUS FOR PREPARING AROMATIC HYDRAZO OR DIAMINODIPHENYL COMPOUNDS

[75] Inventors: Hans de Groot, Nuenen; Eeuwoud van den Heuvel, Helmond; Embrecht Barendrecht, Veldhoven; Leonard J. J. Janssen, Nuenen, all of Netherlands

[73] Assignee: Borma B.V., Netherlands

[21] Appl. No.: 156,339

[22] Filed: Jun. 4, 1980

[30] Foreign Application Priority Data

Jun. 5, 1979 [NL] Netherlands ................. 7904418

[51] Int. Cl.³ ............................................. C25B 3/04
[52] U.S. Cl. ................................................. 204/74
[58] Field of Search ....................................... 204/74

[56] References Cited

U.S. PATENT DOCUMENTS 3,645,864  2/1972  Lawson et al. ................. 204/74

FOREIGN PATENT DOCUMENTS 2026039  12/1970  Fed. Rep. of Germany .
2609530   8/1977  Fed. Rep. of Germany .
1385907  12/1964  France .
  85228   8/1920  Switzerland .
  87885   1/1921  Switzerland .
 484745   2/1977  U.S.S.R. ...................... 204/74

OTHER PUBLICATIONS

Rifi et al., Intro. To Organic Electrochem. pp. 182–189 pub. by Marcel Dekker, Inc. New York (1974).
Dey et al., J. Sci. Ind. Res., vol. 4, pp. 559–568 )1946).
McKee, et al., Trans. Electro Chem. Soc., vol. 68, pp. 329–373 (1935)..
Journal of the Electrochemical Society, vol. 108, No. 4, Apr. 1961, pp. 373–377, K. S. Udupa.
Journal of the Electrochemical Society, vol. 104, No. 8, Aug. 1957, pp. 497–503, Kiichiro Sugino.

Primary Examiner—F. Edmundson
Attorney, Agent, or Firm—Kenyon & Kenyon

[57] ABSTRACT

A method and apparatus for preparing aromatic hydrazo compounds by electrochemical reduction of aromatic nitro compounds on a technical scale. The reaction is carried out continuously and in two steps, comprising a first step in which the aromatic nitro compounds are reduced to form the corresponding azoxy compounds, which are isolated, and a second step in which the azoxy compounds isolated are reduced to form the corresponding hydrazo compounds.

11 Claims, 1 Drawing Figure

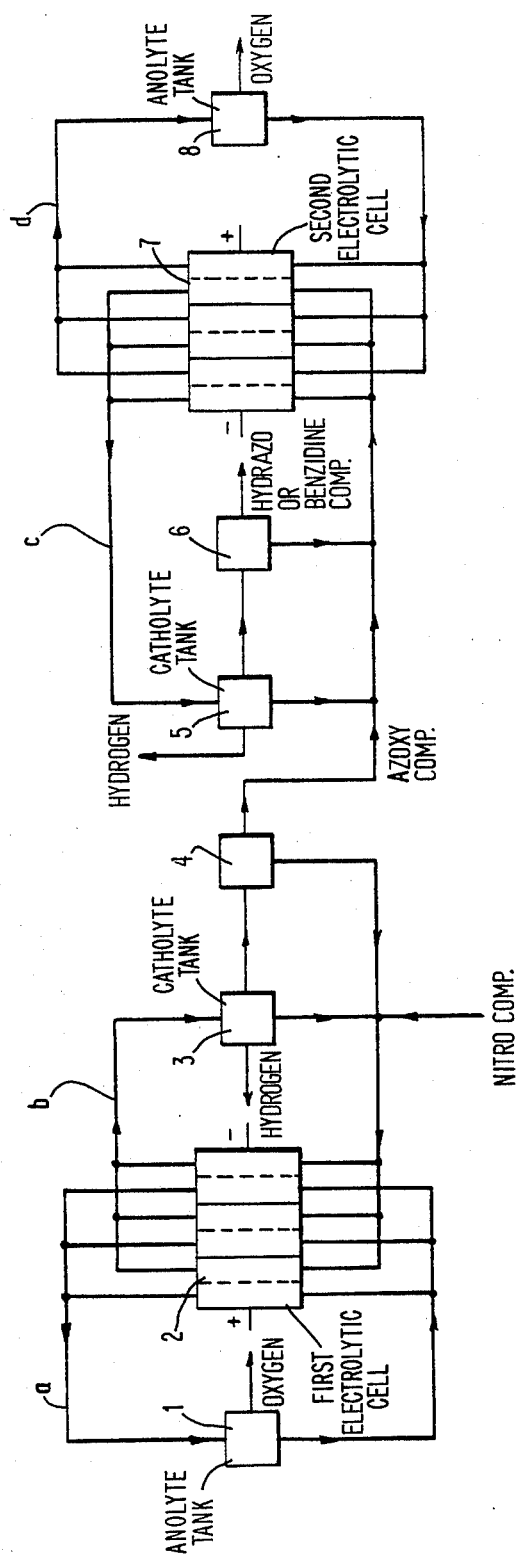

METHOD AND APPARATUS FOR PREPARING AROMATIC HYDRAZO OR DIAMINODIPHENYL COMPOUNDS

This invention relates to a method of preparing aromatic hydrazo or diaminodiphenyl compounds. Aromatic hydrazo compounds, in particular hydrazotoluene, are important starting compounds for dyes, for example for use in the textile industry.

On a technical scale, these compounds have hitherto been prepared by reducing aromatic nitro compounds, in particular o-nitrotoluene, with zinc in an alkaline medium, followed by acidulation after completion of the reduction, whereby the hydrazo compound formed is rearranged to form a diaminodiphenyl compound. This method has major drawbacks. Thus the reduction proceeds in dependence on the quality and form of the zinc to be used. Furthermore, on the ground of both environmental considerations and for reasons of cost price, it is highly desirable to recover the zinc used.

The electrochemical reduction of aromatic nitro compounds, in particular of o-nitrotoluene, is described in the literature (cf J. Sci. Ind. Res. 4, 559 (1946) and Trans. Electrochem. Soc. 68 (1935), 329).

These known methods, in which the reduction of the starting compound is carried out in one step, cannot be used on a technical scale, in particular on account of the formation—to a great extent—of countless by-products.

We have found that the electrochemical reduction of aromatic nitro compounds to form corresponding hydrazo compounds can be carried out on a technical scale without appreciable formation of by-products by carrying out the reaction continuously and in two steps, and isolating the compound formed in the first step before reducing it further.

According to the present invention, therefore, there is provided a method of preparing aromatic hydrazo compounds by electrochemical reduction of aromatic nitro compounds, characterized in that the reaction is carried out continuously in two steps, comprising a first step in which the aromatic nitro compounds are reduced to form the corresponding azoxy compounds, which are isolated, and a subsequent second step, in which said isolated azoxy compounds are reduced to form the corresponding hydrazo compounds.

Subsequently the hydrazo compound formed is converted into the corresponding diaminodiphenyl compound by means of a separate action, or preferably in situ in the cell.

In principle, the method according to the invention can be applied to any aromatic nitro compound. As the reduction of o-nitrotoluene to o-hydrazotoluene (and the subsequent re-arrangement to o-tolidine) is of great practical importance, this reduction will be discussed in particular hereinafter.

The method according to the invention can be carried out in a known per se diaphragm-type electrolytic cell, in which the cathode space is separated from the anode space by a membrane, diaphragm or the like. Preferably an ion-exchanging membrane is used for such separation.

As anolyte, any conventional electrolyte solution, such as a sulphuric acid solution or lye solution is suitable. The choice of the anode material depends on the anolyte used. Thus, for example, nickel may be used when lye is used as the anolyte and platinum-coated titanium when the anolyte contains sulphuric acid.

During the first reduction step, i.e. from the nitro compound to the azoxy compound, the reaction medium in the vicinity of the cathode must be alkaline, because otherwise anilines are formed to a great extent. This means that the average pH of the catholyte may be on the acid side of the neutral range, as, owing to the hydroxyl ion formation and possible hydrogen generation at the cathode, the pH at the cathode will always be slightly higher than the average pH of the reaction medium. Accordingly, the pH of the catholyte is, for example, 4–15, but preferably at least 11.

As catholyte, any suitable electrolyte solution may be used. Preferably, an alcohol/water/lye solution, a water-containing McKee salt (sodium or potassium salt of benzene sulphonic acid)/lye solution or a water-containing lye solution is used. In the two electrolyte solutions first-mentioned, the nitro compound is present in the dissolved state, and in the electrolyte solution last-mentioned in the form of a suspension or emulsion.

As the cathode material for the first reduction step, in principle all electrode materials and, in particular, such as are not corroded in the reaction medium, are suitable. This suitability is further partly dependent on the reaction conditions, such as current density, etc.

Preferably, cathode material is used with which the velocity constant of the reduction reaction of the aromatic nitro compound to the corresponding azoxy compound is considerably higher than the velocity constant of the reduction reaction of the azoxy compound.

In carrying out the method according to the invention, it is important that during the first reduction step, the concentration of the aromatic nitro compound does not decrease below a certain minimum value, because otherwise by-products are formed to an undesirable extent. This minimum value is determined, among other things, by the cathode potential, the nature of the cathode material, convection conditions, temperature, etc.

Accordingly, the method according to the invention is preferably carried out so that during the first reduction step, the concentration of the aromatic nitro compound is kept substantially constant by continuously adding this material. Another reason why this is important is that otherwise at a constant current intensity, there will be a continuously varying cathode potential, which renders it more difficult to cause the reduction to proceed uniformly, partly in view of the relation between the formation of by-products and the cathode potential. The concentration of the aromatic nitro compound is preferably kept equal to the starting concentration.

The consumption of aromatic nitro compound can be determined in various ways, for example by means of the current consumption, with the quantity of coulombs used being determinative of the degree of conversion of the nitro compound. The concentration of nitro compound can also be determined, for example, by liquid-chromatographic analysis of a sample of the reaction solution. During the first reaction step, the concentration of the azoxy compound formed is preferably kept substantially constant by continuously removing this compound. This, too, has a favourable effect on the suppression of the formation of by-products.

The azoxy compound formed during the first reduction step is preferably first purified of any nitro compound that may be present before being converted further during the second reduction step. The advantage is that during the second reduction step there is a slight formation of by-products only.

The second reduction step can be carried out in an electrochemical cell similar to that to be used during the first reduction step. As regards the selection of anolyte and anode material, the same applies as have been observed with regard to the first reduction step.

Although the second reduction step can also be performed in an alkaline medium, an acidic catholyte is preferred. The advantage is that the re-arrangement of the hydrazo compound formed to a diaminodiphenyl compound is effected in situ, and the latter compound is deposited as a salt or basic salt. Thus when o-nitrotoluene is reduced and an acidic medium is used during the second step, o-tolidine is formed in situ, which means a saving of cost in the production of that compound.

A suitable catholyte in the second reduction step is a water/alcohol mixture in which a McKee salt and a McKee acid have been dissolved. In such a catholyte, the azoxy compound is present in the form of a solution, while the diaminodiphenyl compound, formed, for example o-tolidine, forms a salt with the McKee acid. It is also possible to use a water-containing solution of a McKee acid and McKee salt, in which the azoxy compound is present as a suspension or emulsion, depending on the temperature of the catholyte. A further suitable catholyte is an inorganic acid solution of an inorganic salt in water, in which the azoxy compound is also present as a suspension or emulsion. An advantage of using the azoxy compound in the form of such a suspension or emulsion is that the ratio of the diaminodiphenyl compound formed to the less desirable biphenyline isomers is favourable if the reduction is carried out in an alcohol-free medium.

In principle, all corrosion-resistant materials are suitable as cathode materials for the second reduction step. The choice of cathode material is in essence determined by the selection—alkaline or acidic—of the electrolyte. Suitable cathode materials are, for example, platinum, stainless steel, graphite, etc.

The present invention also relates to an apparatus for carrying out the method according to the invention, comprising at least one electrolytic cell with separate cathode and anode spaces for the reduction of the aromatic nitro compound to form the corresponding azoxy compound, and which is coupled to an apparatus for isolating and optionally purifying the azoxy compound formed, and at least one eletrolytic cell having separate anode and cathode spaces for the reduction of the azoxy compound to form the hydrazo compound. The hydrazo compound is subsequently converted into a diaminodiphenyl compound, using the benzidine re-arrangement, either within the cell proper or during a separate after-treatment.

One example of apparatus suitable for use in the method according to the present invention is shown diagrammatically in the accompanying drawing.

Referring now to the drawing, the apparatus shown comprises a first electrolytic cell 2 in which the catholyte continuously circulates in circuit b and the anolyte in circuit a.

The aromatic nitro compound, e.g. o-nitrotoluene, is supplied (preferably) continuously to the catholyte circuit b in order to keep its concentration constant. A small amount of catholyte is passed, preferably continuously, from the catholyte tank 3 to space 4, in which the azoxy compound formed, e.g. o-azoxytoluene, is isolated. This isolation can be effected by crystallization and filtration or, in the case of liquid azoxy compound, e.g. by phase separation. The azoxy compound formed is subsequently supplied to a catholyte circuit c of a second electrolytic cell 7, in which the azoxy compound is supplied to the catholyte. After isolation of the azoxy compound, the catholyte of the first electrolytic cell 2 is regenerated and can subsequently be re-supplied to the catholyte tank 3.

In the second electrolytic cell 7, the catholyte circulates continuously through circuit c and the anolyte through circuit d. A small stream of catholyte is continuously withdrawn from a catholyte tank 5 and supplied to container 6, in which the aromatic hydrazo compound or diaminodiphenyl compound, e.g. o-hydrazotoluene or o-tolidine, is isolated. Also, the catholyte is regenerated in container 6 and is subsequently re-supplied to tank 5.

The invention is illustrated in and by the following examples.

EXAMPLE I

The electrochemical reduction of o-nitrotoluene to azoxytoluene was carried out in an alkaline alcohol/water mixture, using an iron cathode having a surface area of 200 cm$^2$. The anode was a titanium plate having a surface area of 200 cm$^2$ with a platinum/iridium alloy coating thereon. The anolyte was a 1 M $H_2SO_4$ solution and the catholyte an ethanol/water mixture in a weight ratio of 84:16, to which 0.4 mol NaOH and 1.0 mol o-nitrotoluene per liter had been added. o-Nitrotoluene was continuously replenished to keep its concentration constant. The temperature was 50° C. and the current intensity 15 A. The material efficiency for the conversion of o-nitrotoluene to azoxytoluene was found to be 99%, and the current efficiency was determined as 98%.

EXAMPLE II

The electrochemical reduction of o-nitrotoluene to azoxytoluene was carried out in an alkaline aqueous solution to which a McKee salt had been added. The cathode was a platinum plate having a surface area of 30 cm$^2$ and the anode a nickel plate also having an area of 30 cm$^2$. A 4 M KOH solution was used as the anolyte and a solution containing 1 M sodium toluene sulfonate, 0.6 M KOH and 0.2 M to 0.5 M o-nitrotoluene was used as the catholyte. During the electrolysis, o-nitrotoluene was replenished so that its concentration ranged between 0.2 to 0.5 M. The temperature was 60° C. and the current intensity 1 A. The material efficiency was 95% and current intensity 90%.

EXAMPLE III

The electrochemical reduction of azoxytoluene to hydrazotoluene was carried out in an alkaline water/alcohol solution. The anode was a nickel plate having an area of 30 cm$^2$ and the cathode a stainless steel (316) plate also of 30 cm$^2$. A 4 M KOH solution was used as the anolyte and an ethanol/water mixture in a weight ratio of 98:2, containing per liter 2 mols NaOH and 0.2 to 0.05 mol azoxytoluene, was used as the catholyte. Azoxytoluene was continuously replenished during the electrolysis. The temperature was 60° C. and the current intensity averaged 1.3 A over a period of 7 hours.

The azoxytoluene used contained approximately 15% azotoluene. During the electrolysis, the azotoluene concentration remained virtually constant, and azoxytoluene was virtually quantitatively reduced to hydrazotoluene. The current efficiency for the azoxytoluene reduction averaged approximately 70%.

EXAMPLE IV

The electrochemical reduction of 2,2'-dichloroazoxybenzene to 2,2'-dichlorohydrazobenzene and/or 3,3'-dichlorobenzidine was carried out using a gold plate having an area of 60 cm$^2$ as the cathode and a platinum plate having an area of 40 cm$^2$ as the anode. A mixture of ethanol and water (85:15) containing 0.1 M H$_2$SO$_4$ and 0.09 M dichloroazoxybenzene was used as the catholyte and a 2 M H$_2$SO$_4$ solution as the anolyte. Dichloroazoxybenzene was continuously replenished to keep its concentration constant. During this electrolysis, the cathode potential was kept at a constant value of −1050 mV relative to a saturated calomel electrode. The temperature was 60° C. The material efficiency of the dichlorohydrazobenzene formation was found to be 54% and the material efficiency of the 3,3'-dichlorobenzidine formation 42%.

EXAMPLE V

The electrochemical reduction of azoxytoluene to tolidine as carried out in an alcohol/water mixture to which benzenesulfonic acid had been added. A stainless steel (316) plate having an area of 30 cm$^2$ served as the cathode and a platinum plate having an area of 20 cm$^2$ as the anode. The cathlyte was an ethanol/water mixture (90/10) containing 0.5 M benzenesulfonic acid and 0,1 M azoxytoluene. The concentration of azoxytoluene was kept constant by continuous addition thereof. A 2 M H$_2$SO$_4$ solution was used as the anolyte. The current intensity during the electrolysis was 1 A and the temperature was 60° C.

The material efficiency of the o-tolidine formation from azoxytoluene was found to be 78%, and the current efficiency 73%. In the acidic electrolyte (pH approximately 0.5) the o-tolidine formed a salt with the benzenesulfonic acid. The salt formed consisted of 1 mol o-tolidine and 2 mols benzenesulfonic acid. The salt formed was isolated in a conventional manner.

EXAMPLE VI

The electrochemical reduction of azoxytoluene to o-tolidine was carried out in an aqueous solution in which azoxytoluene was emulsified and a McKee acid and McKee salt were dissolved.

A stainless steel plate having a surface area of 30 cm$^2$ was used as the cathode and a platinum plate having a surface area of 20 cm$^2$ as the anode. The catholyte was an aqueous solution in which, per liter, 0.05 mol azoxytoluene was emulsified, and, per liter, 1 mol sodium toluene sulfonate and 0.05 mol toluenesulfonic acid were dissolved. The anolyte was a 2.0 M H$_2$SO$_4$ solution. The electrolysis was carried out at a current intensity of 1.3 A at 60° C. This temperature was higher than the melting point of trans-azoxytoluene, which is approximately 58° C. Through convection of the catholyte, the azoxytoluene remained dispersed in the catholyte in the form of small liquid droplets. The material efficiency for the o-tolidine formation was found to be 90% and the current efficiency 70%. The o-tolidine was subsequently isolated in a conventional manner.

We claim:

1. A method of preparing hydrazo compounds by the electrochemical reduction of aromatic nitro compounds, wherein the reaction is carried out continuously and in two steps, comprising a first step in which the aromatic nitro compounds are reduced to form the corresponding azoxy compounds in a first electrochemical cell, and as the azoxy compounds are produced additional aromatic nitro compound is continuously added to the first electrochemical cell to maintain the concentration of aromatic nitro compound therein substantially constant, and the azoxy compound is continuously removed from the first electrochemical cell to maintain the concentration of azoxy compound therein substantially constant; and subsequently a second step in which the azoxy compounds which have been removed from the first cell are reduced further in a second electrochemical cell to form the corresponding hydrazo compounds.

2. A method as claimed in claim 1, in which the hydrazo compound formed is converted into the corresponding diaminodiphenyl compound in situ in the second electrochemical cell.

3. A method as claimed in claim 1, wherein said first electrochemical cell employs an alkaline catholyte in the reduction to the azoxy compound.

4. A method as claimed in claim 3, in which said catholyte is an alkaline, aqueous solution of a sodium or potassium salt of a benzene or alkylbenzene sulfonic acid.

5. A method as claimed in claim 1 wherein the hydrazo compound formed is converted into the corresponding diaminodiphenyl compound.

6. A method as claimed in claim 1, 2, 3, 4, or 5, wherein the cathode material employed by said second electrochemical cell used during the first reduction step is stainless steel.

7. A method as claimed in claim 1, 2, 3, 4, or 5, wherein the azoxy compound formed and isolated in the first reduction step is purified before being reduced further.

8. A method as claimed in claim 1, 2, 3, 4, or 5, wherein the second reduction step is carried out in an acid medium.

9. A method as claimed in claim 8, wherein the catholyte employed by said second electrochemical cell is an aqueous solution of a sodium or potassium salt of a benzene or alkylbenzene sulfonic acid and a benzene or alkylbenzene sulfonic acid.

10. A method as claimed in claim 1, 2, 3, 4, or 5, wherein the starting compound is o-nitrotoluene.

11. The method according to claim 1, 2, 3, 4 or 10 wherein during the first step aromatic nitro compound is added to the cell to maintain the concentration of the aromatic nitro compound in the first electrochemical cell about equal to its initial concentration.

* * * * *

UNITED STATES PATENT AND TRADEMARK OFFICE
CERTIFICATE OF CORRECTION

PATENT NO. : 4,345,978
DATED : August 24, 1982
INVENTOR(S) : Hans de Groot, et al It is certified that error appears in the above—identified patent and that said Letters Patent is hereby corrected as shown below:

Col. 5, line 22, change "as" to --was--.

Col. 5, line 26, correct spelling of "catholyte".

Col. 6, line 54, change "10" to --5--.

Signed and Sealed this

Sixteenth Day of November 1982

[SEAL]

Attest:

GERALD J. MOSSINGHOFF

*Attesting Officer*     *Commissioner of Patents and Trademarks*